United States Patent [19]

Minowa et al.

[11] Patent Number: 4,510,102

[45] Date of Patent: Apr. 9, 1985

[54] PHOSPHINIC ACID ESTERS AND PROCESS FOR PREPARING THE SAME

[75] Inventors: Nobuto Minowa, Yokohama; Shunzo Fukatsu, Tokyo; Taro Niida, Yokohama; Sadaaki Mase, Tokyo, all of Japan

[73] Assignee: Meiji Seika Kaisha Ltd., Tokyo, Japan

[21] Appl. No.: 458,946

[22] Filed: Jan. 18, 1983

[30] Foreign Application Priority Data

Jan. 29, 1982 [JP] Japan .................................. 57-13985

[51] Int. Cl.$^3$ ................................ C07F 9/32
[52] U.S. Cl. ..................... 260/941; 260/968
[58] Field of Search ................. 260/941, 968

[56] References Cited

FOREIGN PATENT DOCUMENTS 0085391 8/1983 European Pat. Off. ............ 260/941

Primary Examiner—Anton H. Sutto

Attorney, Agent, or Firm—Frishauf, Holtz, Goodman & Woodward

[57] ABSTRACT

Disclosed is a novel process for preparing [(3-amino-3-carboxy)-propyl-1]phosphinic acid derivatives, comprising reacting an alkylalkylphosphonyl halide with a vinylmagnesium halide to form a vinylphosphinic acid derivative, and reacting the vinylphosphinic acid derivative with a Shiff's base to form the aimed product. Also disclosed is a novel intermediate compound formed during the course of the above process, which compound has the general formula:

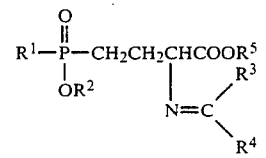

(wherein $R^1$, $R^2$, $R^3$, $R^4$ and $R^5$ are as defined in the specification).

22 Claims, No Drawings

PHOSPHINIC ACID ESTERS AND PROCESS FOR PREPARING THE SAME

The present invention relates to phosphinic derivatives and a novel process for preparing the same. More particularly, it relates to a novel intermediate product of, and a process for preparing, [(3-amino-3-carboxy)-propyl-1]phosphinic acid derivatives which are useful as herbicides and antifungal agents, or starting materials of herbicides and antifungal agents.

Heretofore, the following processes for preparing [(3-amino-3-carboxy)-propyl-1]phosphinic acid derivatives are known:

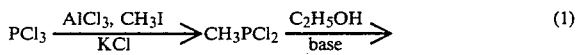 (1)

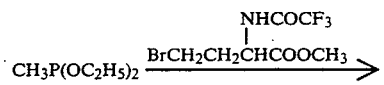

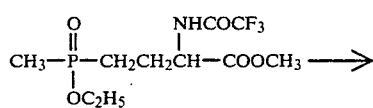

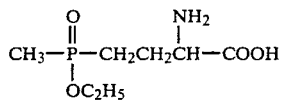

[Helvetica Chimica Acta, 55, 224~239 (1972)]

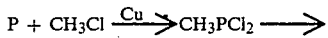 (2)

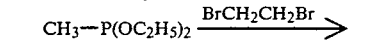

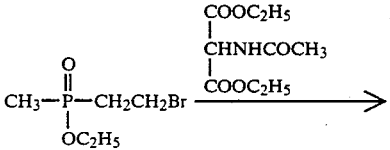

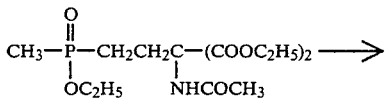

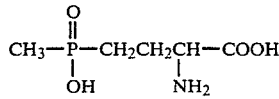

[Japanese Laid-open Patent Application No. 91019/1973]

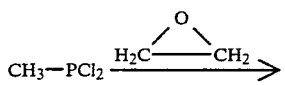 (3)

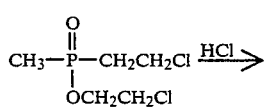

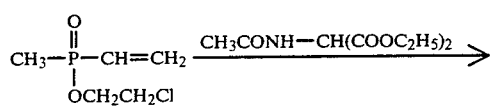

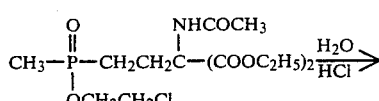

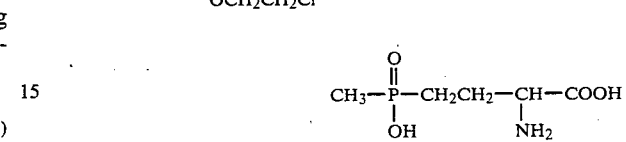

[Journal f. prakt. chemie. Band., 318, Heft 1, 157~160 (1976)]

As shown in the reaction schemes, the prior art processes employ methyldichlorophosphine ($CH_3PCl_2$) as an intermediate compound. This is also the case in the processes disclosed in Japanese Laid-open Patent Applications No. 84529/1979, No. 154715/1979, No. 20714/1980, No. 64596/1980 or the like.

The most significant disadvantage involved in the prior art processes mentioned above resides in the step of producing methyldichlorophosphine, which will be enumerated below:

(a) An industrial production of methyldichlorophosphine on a large scale is difficult.

(b) Methyldichlorophosphine is difficult to handle because of its corrosive property and inflammability upon contact with water. This necessitates complication of reaction facilities.

(c) In the aforementioned process (1), the step of producing methyldichlorophosphine requires a large amount of aluminum chloride and potassium chloride and a high temperature of 110° to 120° C. Further, isolation of the product is difficult and yield of the product is low.

(d) In the aforementioned process (2), the step of producing methyldichlorophosphine requires a high temperature of about 600° C. This tends to lead production of by-products and quite a low yield of the aimed product.

The present inventors have made earnest studies to solve the above-mentioned problems by employing a starting compound other than methyldichlorophosphine. As a result, it was found that alkylalkylphosphonyl halides (I) [Pelchowicz: Organic Phosphorous Compounds, Part I. 238], which may readily and safely be produced in a high yield by utilizing Arbusow reaction as shown in the following reaction schemes, can be used cheaply as the starting material.

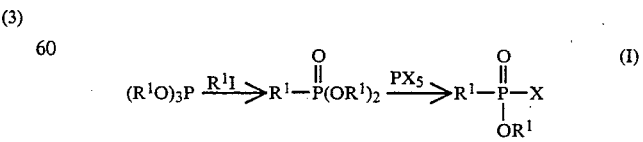 (I)

(wherein, $R^1$ and X are as defined hereinlater).

Heretofore, alkylalkylphosphonyl halides have never been used for the production of the compounds of the present invention. Further, they are rarely reported to have been used for the production of other phosphorus-containing compounds.

Further, the present inventors have studied to explore a process for preparing [(3-amino-3-carboxy)-propyl-1]phosphinic acid derivatives cheaply with small numbers of reaction steps and on a large scale. As a result, it was found that glycine or its ester which is quite cheaply available is reacted with an aldehyde or a ketone in the presence of a base to give a Schiff's base easily, and that the Schiff's base may be used as an intermediate compound for producing the final product.

It is an object of the invention to provide an industrially superior process for producing [(3-amino-3-carboxy)-propyl-1]phosphinic acid derivatives (V) that employs a readily producible alkylalkylphosphonyl halide as the starting material.

It is another object of the invention to provide a novel intermediate product formed during the course of the above-mentioned process.

The present invention is to provide a process for preparing [(3-amino-3-carboxy)-propyl-1]phosphinic acid derivatives represented by the formula (V):

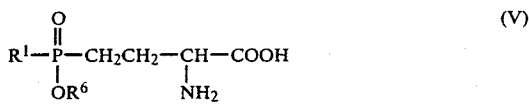

(wherein, $R^1$ represents a straight or branched chain alkyl group having from 1 to 5 carbon atoms, an aryl group or an aralkyl group and $R^6$ represents a hydrogen atom, a straight or branched chain alkyl group having from 1 to 5 carbon atoms, an aryl group or an aralkyl group)
by reacting a compound represented by the formula (I):

(wherein, $R^2$ represents a straight or branched chain alkyl group having from 1 to 5 carbon atoms, an aryl group or an aralkyl group)
with a compound represented by the formula (II):

$$CH_2=CHMgX'$$ (II)

(wherein, $X'$ represents a chlorine atom or a bromine atom)
to give a compound represented by the formula (III):

(wherein, $R^1$ and $R^2$ are as defined above),
then by reacting the resulting compound (III) with a compound represented by the formula (IV):

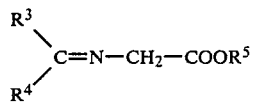

(wherein, $R^3$ and $R^4$ are same or different and $R^3$, $R^4$ and $R^5$ each represent a hydrogen atom, a straight or branched chain alkyl group having from 1 to 5 carbon atoms, an aryl group or an aralkyl group, provided that $R^3$ and $R^4$ are not hydrogen atoms at the same time)
in the presence of a base, and finally by subjecting the thus produced compound to hydrolysis.

The process according to the present invention will be explained in detail in the order of each step.

First step: (I)+(II)→(III)

In the formula (I), the straight or branched chain alkyl group having from 1 to 5 carbon atoms for the groups $R^1$ and $R^2$ includes, for example, a methyl, ethyl, propyl, isopropyl, butyl and t-butyl. The aryl group includes, for example, a phenyl, chlorophenyl, nitrophenyl and methoxyphenyl. The aralkyl group includes, for example, a benzyl.

The alkylalkylphosphonyl halide represented by the formula (I) may be exemplified, for example, by a methylmethylphosphonyl chloride, ethylethylphosphonyl chloride and phenylphenylphosphonyl chloride.

The vinylmagnesium halide represented by the formula (II) may be exemplified, for example, by a vinylmagnesium chloride and vinylmagnesium bromide.

In the step, the compound (I) is dissolved in a usual organic solvent such as tetrahydrofuran, dioxane or dimethoxyethane and the solution is cooled to a low temperature, preferably to $-10°$ to $-70°$ C. To the solution is added a solution of the compound (II) in an organic solvent (such as tetrahydrofuran, dimethoxyethane or dioxane), then the reaction mixture is adjusted to a temperature of $-15°$ to $20°$ C. to complete the reaction.

The time required for the reaction will vary over a wide range, depending on the natures of starting material and reagents, reaction temperature and moles of compounds used, but will normally be within a period of 0.5 to 48 hours, preferably 3 to 12 hours.

The molar ratio of the compound (II) to the compound (I) is within a range of 1 to 5 moles, preferably 1 to 2 moles.

The amount of solvent is within a normal range used for the purpose.

After completion of the reaction a small amount of water or an aqueous solution of a base is added to the reaction solution to decompose unreacted compounds. Alternatively, solvent employed is distilled out without addition of water. The organic layer is then extracted from a water and an organic solvent system (methylene chloride, chloroform, ethyl acetate, toluene and diethyl ether are exemplified for the organic solvent) and the extract is washed with water and dried.

In the second step, a solution containing the compound (III) may be used as such. Alternatively, after the solvent is distilled off, the compound (III) may be used after purifying it, for instance, by distillation.

The vinylphosphinic acid derivative represented by the formula (III) may be exemplified, for example, by methyl methylvinylphosphinate, ethyl ethylvinylphosphinate and phenyl phenylvinylphosphinate.

Second step: (III)+(IV)→(V)

The vinylphosphinic acid derivative represented by the formula (III) is a reaction product of the first step.

In the formula (IV), the straight or branched chain alkyl group having from 1 to 5 carbon atoms for the groups $R^3$ and $R^4$ includes, for example, a methyl, ethyl, propyl, isopropyl, butyl and isobutyl. The aryl group includes, for example, a phenyl, chlorophenyl, nitrophenyl and methoxyphenyl. The aralkyl group includes, for example, a benzyl.

The alkyl group having from 1 to 5 carbon atoms for the group $R^5$ includes, for example, a methyl, ethyl, propyl, butyl and t-butyl. The aryl group includes, for example, a phenyl, chlorophenyl, nitrophenyl and methoxyphenyl. The aralkyl group includes, for example, a benzyl.

The Schiff's base represented by the formula (IV) may be exemplified, for example, by ethyl 2-(phenylmethylene)aminoacetate.

In the step, the compounds (III) and (IV) are first reacted in the presence of a base.

Such a base includes, for example, sodium methylate, sodium ethylate, sodium hydroxide and potassium hydroxide.

Normally, the reaction is effected in an organic solvent such as methanol, ethanol, toluene, dimethoxyethane or tetrahydrofuran.

The temperature at which the reaction is carried out is in the range from $-50°$ to $50°$ C., preferably $-10°$ to $10°$ C.

The time required for the reaction is within a range of 0.5 to 24 hours.

The molar ratio of the compound (IV) to the compound (III) is within a range of 1 to 3 moles, whereas the alkali is used in 0.01 to 3.0 molar equivalents, preferably 0.1 to 1.0 molar equivalent, based on 1 molar equivalent of the compound (III).

The amount of solvent is within a normal range used for this purpose.

Thus, there is produced an intermediate compound represented by the formula (V'):

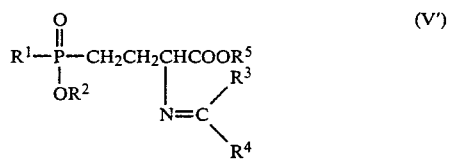

(wherein, $R^1$, $R^2$, $R^3$, $R^4$ and $R^5$ are as defined above), which is novel by itself, and may be transformed, without isolation, to the compound (V) by means of a conventional deprotecting method such as hydrolysis.

Namely, a mineral acid such as hydrochloric acid or sulfuric acid is added to the reaction mixture containing the compound (V') then the mixture is heated. Alternatively, the solvent is distilled off from the reaction mixture and the organic layer is extracted from a water and organic solvent system (methylene chloride, chloroform, ethyl acetate, toluene and diethyl ether are exemplified as the organic solvent), then the extract, which may be concentrated, is heated with a mineral acid to give the compound (V).

The mineral acid is employed in an exessive amount, for example, 30 molar times the compound (V'). The temperature at which the reaction is carried out is within a range from 20° to 150° C. The time required for the reaction is within a range of from 0.5 to 24 hours.

The hydrolysis may also be effected by a combination of alkaline hydrolysis and/or acidic hydrolysis.

After completion of the reaction, the compound (V) may be isolated by the conventional neutralization and purification.

Where the product is further purified, it may be performed, for example, by chromatography using a strongly acidic ion-exchange resin.

The compound (V), if desired, may be derived to its salt, such as sodium, potassium or ammonium salt. Further, it may be derived to its acid-addition salt.

In the formula (V), the alkyl group having from 1 to 5 carbon atoms includes, for example, a methyl, ethyl, propyl, isopropyl, butyl and t-butyl. The aryl group includes, for example, a phenyl, chlorophenyl, nitrophenyl and methoxyphenyl.

The aralkyl includes, for example, a benzyl.

The [(3-amino-3-carboxy)-propyl-1]phosphinic acid derivatives represented by the formula (V) may be exemplified, for example, by 3-amino-3-carboxypropylmethylphosphinic acid, 3-amino-3-carboxypropyl-ethylphosphinic acid and 3-amino-3-carboxypropyl-phenylphosphinic acid.

The [(3-amino-3-carboxy)-propyl-1]phosphinic acid derivative (V) prepared by the process of the invention is in the racemic form. If necessary, it may be optically resolved for use.

One of the compounds of formula (V), that is [(3-amino-3-carboxy)-propyl-1]methylphosphinic acid is useful as herbicide.

The compound (V) is also useful as an additive to a culture medium, when preparing the SF-1293 substance which is useful as herbicide (Japanese Patent Publication No. 639/1976).

The process of the invention is to react the alkylalkylphosphonyl halide (I) with the vinylmagnesium halide (II) to give the vinylphosphinic acid derivative (III), then react the compound (III) with the Schiff's base (IV) in the presence of a base, and finally subject the resulting product (V') to hydrolysis to give the [(3-amino-3-carboxy)-propyl-1]phosphinic acid derivative (V).

The present process is an extremely superior industrial method for producing the compound (V), cheaply and safely, in a small number of steps on a large scale, as compared with the prior art processes.

The present invention will be explained in more detail by the following examples, which, however, should not be construed to limit the scope of the invention.

EXAMPLE 1

(A) Preparation of methyl methylvinylphosphinate:

10.0 g of methylmethylphosphonyl chloride were dissolved in 20 ml of tetrahydrofuran (THF). The solution was cooled to −50° C., then a solution of 10.2 g of vinylmagnesium bromide in 25 ml of THF were added dropwise. Upon completion of addition, the temperature of the reaction mixture was elevated up to 0° C., then 20 ml of a saturated aqueous solution of ammonium chloride were added. The solution was concentrated by evaporation, extracted with dichloromethane and the extract was dried over anhydrous magnesium sulfate. The extract was subjected to distillation in vacuo to give 5.61 g of the desired product boiling at 74° to 76° C./14 mmHg (60.0% yield).

(B) Preparation of 3-amino-3-carboxypropyl-methylphosphinic acid:

(i) 19.2 mg of metallic sodium were dissolved in 5.0 ml of ethanol and the solution was cooled to −10° C. 637 mg of ethyl 2-(phenylmethylene)aminoacetate and then 400 mg of methyl methylvinylphosphinate were added to the solution. The reaction mixture was stirred at −10° C. for 5 hours then 5 ml of 1N hydrochloric acid were added and the mixture was concentrated. 10 ml of a concentrated hydrochloric acid were added to the residue and then the mixture was refluxed for 6 hours, with stirring. The reaction mixture was concentrated, to which 5 ml of propylene oxide were added, then the mixture was stirred for a further 1 hour. Upon completion of stirring, the reaction mixture was concentrated and the resulting crude product was purified through an ion-exchange resin, Dowex 50WX$_2$ (trade name) to give 302 mg of crystalline powder of the desired product melting at 227° to 229° C. (50.1% yield).

(ii) 149 mg of tert-butoxy potassium were dissolved in 5.0 ml of tetrahydrofuran and the solution was cooled to −10° C. 1.07 g of ethyl N-(diphenylmethylene)-glycinate and then 400 mg of methyl methylvinylphosphinate were added to the solution. The reaction mixture was stirred at −10° C. for 4 hours and then the solvent was distilled off in vacuo. To the resulting residue were added 10 ml of a concentrated hydrochloric acid and then the mixture was refluxed for 6 hours with stirring. The reaction mixture was concentrated, to which 5 ml of propylene oxide were added, then the mixture was stirred for a further 1 hour. Upon completion of stirring, the reaction mixture was concentrated and the resulting crude product was purified through an ion-exchange resin, Dowex 50WX$_2$ (trade name, available from Dow Chemical Co., U.S.A.), to give 315.5 mg of crystalline powder of the desired product, melting at 227° to 229° C. (52.3% yield).

(iii) 795 mg of ethyl 2-(phenylmethylene)aminoacetate were added to 5.0 ml of ethanol, to which further added were 47 mg of potassium hydroxide and 500 mg of methyl methylvinylphosphinate. The reaction mixture was stirred at 25° C. for 2 hours, and then the solvent was distilled off in vacuo. To the resulting residue were added 10 ml of 6N hydrochloric acid and the mixture was refluxed for 30 hours with stirring. The reaction mixture was concentrated, to which 5.0 ml of propylene oxide were added, then the mixture was stirred for a further 1 hour. Upon completion of stirring, the reaction mixture was concentrated and the resulting crude product was purified through an ion-exchange resin, Dowex 50WX$_2$ (trade name), to give 490 mg of crystalline powder of the desired product, melting at 227° to 229° C.

EXAMPLE 2

(A) Preparation of ethyl ethylvinylphosphinate:

7.75 g of ethylethylphosphonyl chloride were dissolved in 15 ml of THF, and the solution was cooled to −50° C. To the solution was added dropwise a solution of 7.14 g of vinylmagnesium bromide in 20 ml of THF. After completion of addition, the reaction mixture was warmed up to 0° C., then treated in the similar manner as in Example 1 (A) to give 4.23 g of the desired product boiling at 86.5° C./14 mmHg (58.0% yield).

(B) Preparation of 3-amino-3-carboxypropylethylphosphinic acid:

43.6 mg of metallic sodium were dissolved in 5.0 ml of ethanol and the solution was cooled to 0° C. 363 mg of ethyl 2-(phenylmethylene)aminoacetate and then 255 mg of ethyl ethylvinylphosphinate were added to the solution, and the mixture was stirred at 0° C. for 6 hours. The reaction mixture was then treated in the similar manner as in Example 1 (B)-(i) to give 113 mg of the desired product melting at 183° to 186° C. (30.5% yield).

EXAMPLE 3

(A) Preparation of phenyl phenylvinylphosphinate:

9.74 g of phenylphenylphosphonyl chloride were dissolved in 20 ml of THF and the solution was cooled to −50° C. To the solution was added dropwise a solution of 6.71 g of vinylmagnesium bromide in 25 ml of THF, then the reaction mixture was warmed up to 0° C. The mixture was then treated in the similar manner as in Example 1 (A) to give 5.15 g of the desired product boiling at 130° to 133° C./1 mmHg (55.3% yield).

(B) Preparation of 3-amino-3-carboxypropyl-phenylphosphinic acid:

41.4 mg of metallic sodium were dissolved in 5.0 ml of ethanol and the solution was cooled to 0° C. 345 mg of ethyl 2-(phenylmethylene)aminoacetate and then 328 mg of phenyl phenylvinylphosphinate were added to the solution, and the mixture was stirred at 0° C. for 6 hours.

The reaction mixture was then treated in the similar manner as in Example 1 (B) to give 142 mg of the desired compound (V) melting at 233° to 236° C. (32.4% yield).

EXAMPLE 4

Preparation of the compound of the formula (V'):

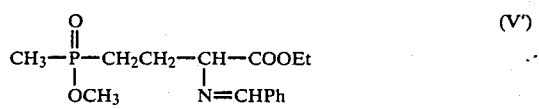

19.2 mg of metallic sodium were added to and dissolved in 5.0 ml of ethanol and the solution was cooled to −10° C. 637 mg of ethyl 2-(phenylmethylene)aminoacetate and then 400 mg of methyl methylvinylphosphinate obtained according to Example 1 (A) were added to the solution. The reaction mixture was stirred at −10° C. for 5 hours, followed by distillation of the solvent in vacuo. To the resulting residue were added 10 ml of chloroform, which was then washed by an aqueous solution of saturated ammonium choride and an aqueous solution of saturated sodium chloride, and dried over magnesium sulfate. After drying, magnesium sulfate was filtered out, and the filtrate was concentrated in vacuo. The resulting residue was subjected to a column chromatography (employing 7.0 g of Kieselgel 100, trade name, available from Merck AG., 70 to 230 mesh; solvent of chloroform:methanol=20:1) to concentrate in vacuo the portions corresponding to fractions 14 and 15 (10 ml each), whereby 413 mg of compound (V') were obtained.

The compound of the formula (V') (wherein $R^1$=CH$_3$, $R^2$=CH$_3$, $R^5$=ethyl, $R^3$=H, $R^4$=phenyl) may be separated by using Kiesegel 100 column chromatography (70 to 230 mesh, solvents of chloroform-:methanol=20:1).

NMR (CDCl$_3$) δ ppm: 1.27 (t, 3H, J=7.5 Hz), 1.47 (d, 3H, JpH=14 Hz), 1.5~2.7 (m, 4H), 3.66 (d, J=10.5 Hz) } 3H in
3.69 (d, J=10.5 Hz) } total 4.02 (t, 1H, J=7.0 Hz), 4.20 (q, 2H, J=7.5 Hz), 7.2~7.9 (m, 5H), 8.30 (s, 1H).

FD mass: (m/e) 312 (M+1)

IR: 1730 cm$^{-1}$ (—COOEt)
1635 cm$^{-1}$ (—C=N—)

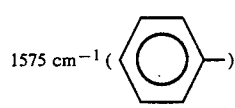
1575 cm$^{-1}$ 1210 cm$^{-1}$ (P=O)

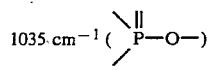
1035 cm$^{-1}$

We claim:

1. A compound represented by the formula (V'):

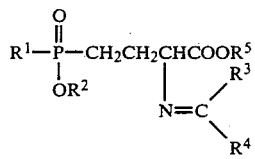

wherein R$^1$ and R$^2$ are same or different and each represent a straight or branched chain alkyl group having from 1 to 5 carbon atoms, an aryl group or an aralkyl group, R$^3$ and R$^4$ are same or different and R$^3$, R$^4$ and R$^5$ each represent a hydrogen atom, a straight or branched chain alkyl group having from 1 to 5 carbon atoms, an aryl group or an aralkyl group, provided that R$^3$ and R$^4$ are not hydrogen atoms at the same time.

2. A process for preparing a compound represented by the formula (V'):

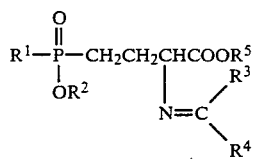

wherein R$^1$ and R$^2$ are same or different and each represent a straight or branched chain alkyl group having from 1 to 5 carbon atoms, an aryl group or an aralkyl group, R$^3$ and R$^4$ are same or different and R$^3$, R$^4$ and R$^5$ each represent a hydrogen atom, a straight or branched chain alkyl group having from 1 to 5 carbon atoms, an aryl group or an aralkyl group, provided that R$^3$ and R$^4$ are not hydrogen atoms at the same time, which comprises the steps of; reacting a compound represented by the formula (I):

wherein, R$^1$ and R$^2$ are as defined above, and
X represents a chlorine atom or a bromine atom, with a compound represented by the formula (II):

wherein, X' represents a chlorine atom or a bromine atom,
to give a compound having the formula (III):

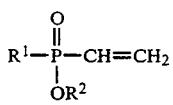

wherein, R$^1$ and R$^2$ are as defined above,
reacting the compound having the formula (III) with a compound represented by the formula (IV):

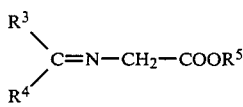

wherein, R$^3$, R$^4$ and R$^5$ are as defined above,
in the presence of a base.

3. The process according to claim 2, wherein said compounds of the formulae (I) and (II) are dissolved in an organic solvent cooled to a temperature of from −10° to −70° C. and then reacted at a temperature of from −15° to 20° C. for 0.5 to 48 hours.

4. The process according to claim 2, wherein said compound of the formula (II) is used in 1 to 5 moles relative to the compound of the formula (I).

5. The process according to claim 2, wherein said compounds of the formulae (III) and (IV) are reacted at a temperature of from −50° to 50° C. for 0.5 to 24 hours.

6. The process according to claim 2, wherein the compound of the formula (IV) is used in 1 to 3 moles relative to the compound of the formula (III).

7. The process according to claim 2, wherein said base is one selected from the group consisting of sodium methylate, sodium ethylate, sodium hydroxide and potassium hydroxide, and is used in 0.01 to 3 molar equivalents relative to 1 molar equivalent of the compound of the formula (III).

8. The process according to claim 2, wherein the reaction is carried out in an organic solvent selected from the group consisting of methanol, ethanol, toluene, dimethoxyethane and tetrahydrofuran.

9. A process for preparing a compound represented by the formula (V'):

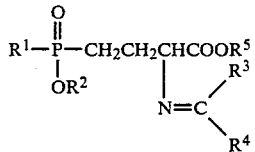

wherein $R^1$ and $R^2$ are same or different and each represent a straight or branched chain alkyl group having from 1 to 5 carbon atoms, an aryl group or an aralkyl group, $R^3$ and $R^4$ are same or different and $R^3$, $R^4$ and $R^5$ each represent a hydrogen atom, a straight or branched chain alkyl group having from 1 to 5 carbon atoms, an aryl group or an aralkyl group, provided that $R^3$ and $R^4$ are not hydrogen atoms at the same time, which comprises the step of; reacting a compound represented by the formula (III):

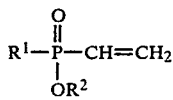
(III)

wherein, $R^1$ and $R^2$ are as defined above,
with a compound having the formula (IV):

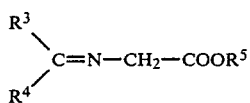
(IV)

wherein, $R^3$, $R^4$ and $R^5$ are as defined above
in the presence of a base.

10. The process according to claim 9, wherein said compounds of the formulae (III) and (IV) are reacted at a temperature of from $-50°$ to $50°$ C. for 0.5 to 24 hours.

11. The process according to claim 9, wherein the compound of the formula (IV) is used in 1 to 3 moles relative to the compound of the formula (III).

12. The process according to claim 9, wherein said base is one selected from the group consisting of sodium methylate, sodium ethylate, sodium hydroxide and potassium hydroxide, and is used in 0.01 to 3 molar equivalents relative to 1 molar equivalent of the compound of the formula (III).

13. The process according to claim 9, wherein the reaction is carried out in an organic solvent selected from the group consisting of methanol, ethanol, toluene, dimethoxyethane and tetrahydrofuran.

14. The compound of claim 1 wherein said aryl group is a phenyl group and said aralkyl group is a benzyl group.

15. The process according to claim 2, wherein said aryl group is a phenyl group and said aralkyl group is a benzyl group.

16. The process according to claim 15, wherein said compounds of the formulae (I) and (II) are dissolved in an organic solvent cooled to a temperature of from $-10°$ to $-70°$ C. and then reacted at a temperature of from $-15°$ to $20°$ C. for 0.5 to 48 hours and wherein said compound of the formula (II) is used in 1 to 5 moles relative to the compound of the formula (I).

17. The process according to claim 16, wherein said compounds of the formulae (III) and (IV) are reacted at a temperature of from $-50°$ to $50°$ C. for 0.5 to 24 hours and wherein the compound of the formula (IV) is used in 1 to 3 moles relative to the compound of the formula (III).

18. The process according to claim 17, wherein said base is selected from the group consisting of sodium methylate, sodium ethylate, sodium hydroxide and potassium hydroxide, and is used in 0.01 to 3 molar equivalents relative to 1 molar equivalent of the compound of the formula (III) and wherein the reaction is carried out in an organic solvent selected from the group consisting of methanol, ethanol, toluene, dimethoxyethane and tetrahydrofuran.

19. The process according to claim 9 wherein said aryl group is a phenyl group and said aralkyl group is a benzyl group.

20. The process according to claim 19, wherein said compounds of the formulae (III) and (IV) are reacted at a temperature of from $-50°$ to $50°$ C. for 0.5 to 24 hours and wherein the compound of the formula (IV) is used in 1 to 3 moles relative to the compound of the formula (III).

21. The process according to claim 20, wherein said base is selected from the group consisting of sodium methylate, sodium ethylate, sodium hydroxide and potassium hydroxide, and is used in 0.01 to 3 molar equivalents relative to 1 molar equivalent of the compound of the formula (III) and wherein the reaction is carried out in an organic solvent selected from the group consisting of methanol, ethanol, toluene, dimethoxyethane and tetrahydrofuran.

22. The process according to claim 19, wherein said base is selected from the group consisting of sodium methylate, sodium ethylate, sodium hydroxide and potassium hydroxide, and is used in 0.01 to 3 molar equivalents relative to 1 molar equivalent of the compound of the formula (III) and wherein the reaction is carried out in an organic solvent selected from the group consisting of methanol, ethanol, toluene, dimethoxyethane and tetrahydrofuran.

* * * * *